United States Patent [19]
Bruchmann et al.

[11] Patent Number: 5,917,059
[45] Date of Patent: Jun. 29, 1999

[54] PREPARATION OF CYCLIC ACETALS OR KETALS

[75] Inventors: Bernd Bruchmann, Freinsheim; Karl Häberle, Speyer; Helmut Gruner, Schwarzheide; Michael Hirn, Mannheim, all of Germany

[73] Assignee: BASF Aktiengesellschaft, Ludwigshafen, Germany

[21] Appl. No.: 08/969,775

[22] Filed: Nov. 13, 1997

[30] Foreign Application Priority Data

Nov. 15, 1996 [DE] Germany ............... 196 47 395

[51] Int. Cl.⁶ .................. C07D 317/12; C07D 317/20; C07D 319/06
[52] U.S. Cl. .............. 549/372; 549/374; 549/430; 549/449; 549/453
[58] Field of Search ................... 549/372, 374, 549/430, 449, 453

[56] References Cited

U.S. PATENT DOCUMENTS 5,191,069  3/1993  Roeschert et al. .................. 534/556

FOREIGN PATENT DOCUMENTS 456 073  4/1991  European Pat. Off. .

OTHER PUBLICATIONS

Chem. Abst., vol. 97, No. 7, 1982, AN 55794V.
Chem. Abst., vol. 76, No. 23, 1972, AN 139926u.
J. of Org. Chem., vol. 48, No. 26, Dec. 30, 1983, pp. 5214–5221.
Zeit. fur Chem., vol. 26, No. 3, Mar. 1986, pp. 97–98.

Primary Examiner—Ba K. Trinh
Attorney, Agent, or Firm—Keil & Weinkauf

[57] ABSTRACT

Cyclic acetals or ketals are prepared by reacting a polyol with the appropriate aldehydes or ketones, with part of the aldehyde or ketone being distilled out during the reaction.

5 Claims, No Drawings

PREPARATION OF CYCLIC ACETALS OR KETALS

The invention relates to a process for preparing cyclic acetals and ketals by reacting a polyol with an excess of an aldehyde or ketone having 1 to 6 carbon atoms.

The preparation of cyclic acetals, eg. of 2,2-dimethyl-4-methylol-1,3-dioxolane, by reacting, for example, glycerol with aldehydes (eg. formaldehyde) or ketones (eg. acetone or methyl ethyl ketone) with acid catalysis has been known for a long time. A problem in every preparation process is the removal of the water of reaction and prevention of an intermolecular reaction of the alcohols with the aldehydes or ketones, which leads to formation of oligomers and thus reduces the yield of cyclic acetals (see reference [1] in this connection).

Both batchwise and continuous production processes are customary, with batchwise ones predominating. Thus, reference [2] describes a batchwise process for preparing isopropylideneglycerol (IPG) from glycerol and acetone in the molar ratio 1:1.1 with the addition of an acid catalyst without a water entrainer. In this process, glycerol and acetone react to the equilibrium concentration. The mixture is then heated, and the water of reaction is removed under 0.01333 bar (10 torr). The residue is then distilled under 0.00667 bar (5 torr) in order to obtain the required product. The stated yield of IPG is 80%. The disadvantage of this process is that the yield of IPG can never exceed the concentration predetermined by the reaction equilibrium. With the stated ratio of acetone to glycerol there is likewise expected to be an intermolecular reaction to a marked extent. It is also a disadvantage that an apparatus designed for reduced pressure is required.

A similar process is described in reference [3]. In this case, glycerol or trimethylolpropane (TMP) is heated with an excess of acetone with p-toluenesulfonic acid as catalyst. After neutralization and filtration, the product of the reaction is purified by) distillation. The yields amount to 56%.

The use of entrainers for removing the water of reaction is customary and is described, for example, in reference [1]. Reference [4] also describes very generally a process for preparing cyclic ketals from glycerol and n-alkyl methyl ketones, eg. 2-butanone or 2-hexanone. In this case, glycerol, the appropriate ketone, benzene and p-toluenesulfonic acid are heated together. The benzene acts as entrainer for the water produced in the reaction. The stated yield is 85 mol %. However, this process is unsuitable for using acetone as ketone because acetone is removed by distillation even before the benzene and is thus removed from the actual reaction. The yields of cyclic ketals in this case are very small.

Hence entrainers for water used when glycerol is reacted with acetone are petroleum ethers or else chloroform (see references [5] to [7]). However, the efficiency of these solvents is not particularly high because they are very miscible with acetone. This considerably impairs separation of the aqueous phase from the organic solvent mixture and results in the water of reaction being incompletely removed azeotropically, which is also evident from the very long reaction time (43 h in the case of petroleum ether, reference [6]).

The removal of the water of reaction in situ by desiccants has likewise been described. References [8] and [9] mention sodium sulfate and phosphorus pentoxide, which also act as catalysts. Molecular sieves have also been used more recently (reference [10]). These processes are unsuitable for the industrial scale because the desiccant either results as waste product or must undergo elaborate regeneration.

In order to avoid problems in the preparation of isopropylidene glycerol in a batch process, technically elaborate continuous preparation processes have been described. In reference [11], the reaction of glycerol with acetone with acid catalysis is carried out only to the equilibrium concentration (about 45% IPG). After inactivation of the catalyst, water, acetone, IPG and glycerol are separated by distillation, and the unreacted glycerol and acetone are returned to the reaction. However, the inactivated catalyst remains in the glycerol and may cause side reactions. The same author therefore proposes in reference [12] an acidic fixed bed ion exchanger as catalyst, in which case neutralization is unnecessary. In both these methods ([11] and [12]), as a consequence of the incomplete conversion, glycerol is subject to great thermal stress as the bottom product in the distillation. This leads to byproducts which, in a continuous process, must be removed and may thus considerably reduce the yields. In addition, the reaction procedure is necessarily elaborate because of the workup of the products under reduced pressure.

It is an object of the present invention to provide a process for preparing cyclic acetals or ketals which is simple to carry out even with aldehydes or ketones which are at least partially miscible with water and/or have a boiling point which is in the region of the boiling point of water or below.

We have found that this object is achieved by employing the aldehyde or ketone in excess and removing the aldehyde or ketone by distillation during the reaction.

The present invention therefore relates to a, preferably batchwise, process for preparing cyclic acetals or ketals by reacting a polyol with an excess of an aldehyde or a ketone having 1 to 6 carbon atoms, wherein aldehyde or ketone is distilled out during the reaction.

Aldehydes or ketones (also referred to as carbonyl compounds hereinafter) which can be used are, in particular, those whose boiling point under atmospheric pressure is <110° C. and preferably <100° C. Carbonyl compounds having 1 to 4 carbon atoms are particularly preferred, especially acetone, 2-butanone, formaldehyde, acetaldehyde or propionaldehyde.

It has surprisingly emerged that the carbonyl compound is not only a reactant but also acts as medium for transporting the water produced in the reaction, although the carbonyl compounds are at least partially, or even completely (such as acetone, methyl ethyl ketone, formaldehyde, acetaldehyde), miscible with water and do not form an azeotrope under the distillation conditions. Nevertheless, the water which is formed is removed in this way from the equilibrium so that high yields of cyclic compounds are obtained.

It has proven expedient in the process according to the invention to replace the carbonyl compound distilled out during the reaction by fresh carbonyl compound, ie. one with a water content $\leq 1\%$ and, in particular, $\leq 0.8\%$. The replacement of the carbonyl compound can take place by stepwise addition or, preferably, continuous addition to the reaction mixture. This expediently takes place in accordance with the rate of evaporation, ie. the amount of carbonyl compound in the reaction mixture is kept constant. The carbonyl compound which is distilled out can be dried in a conventional way, for example by distillation or by absorption of the water on desiccants, and be reused.

It is preferable not to distil the carbonyl compound out throughout the reaction but only to start the distillation after a considerable amount of the acetal or ketal has formed. It is expedient to start as soon as the reaction equilibrium has been set up.

The amount of carbonyl compound can vary within a wide range. An excess of at least 10 mol %, based on the amount of polyol, is generally used. It is preferred to use from 2 to 30 mol, in particular 3 to 15 mol, of carbonyl compound per mole of polyol.

It is possible to use as polyol all compounds which have at least two hydroxyl groups in a position leading to the formation of a cyclic acetal or ketal having 5 to 8 and, in particular, 5 or 6 ring atoms. Polyols which can be used are:

aliphatic diols whose hydroxyl groups are in positions 1,2, 1,3, 1,4 or 1,5. Examples thereof are ethylene glycol, 1,2-propylene glycol, 1,3-propylene glycol, 1,2-butanediol, 1,3-butanediol, 1,4-butanediol, 1,5-pentanediol, neopentyl glycol etc.;

aromatic diols such as 1,2-dihydroxybenzene;

aliphatic triols such as glycerol, trimethylolpropane, trimethylolethane or trimethylolmethane;

aliphatic tetrols such as pentaerythritol;

sugar alcohols having 4 to 6 hydroxyl groups, such as threitol, erythritol, xylitol, dulcitol, mannitol and sorbitol;

sugars such as aldoses and ketoses, for example glucose, mannose, fructose, etc.

Diols or triols having 2 to 12 carbons are preferred, especially ethylene glycol, 1,2- and 1,3-propylene glycol, glycerol and trimethylolpropane.

The reaction is generally carried out at from about 20° C. to the boiling point of the reaction mixture. The reaction time depends on the reaction temperature and the ratios of amounts of the starting materials. It is, in general, from about 20 min to 48 h.

All the catalysts which can be used for preparing acetals or ketals can be employed, eg. acids such as toluenesulfonic acid, sulfuric acid, hydrogen chloride and acidic ion exchangers etc.

The amount of catalyst is generally from 0.01 to 0.5 mol % based on the alcohol.

The products of the intramolecular reaction, namely cyclic acetals and ketals, are obtained in high purities, namely from 95 to 99.5%, in the process according to the invention. Such purities are sufficient for many applications so that further workup of the reaction product, eg. by distillation, is unnecessary, especially in the preparation of isopropylidene glycerol.

The following Examples illustrate the invention without restricting it.

EXAMPLES 0.05 mol % of p-toluenesulfonic acid monohydrate, based on alcohol, was added to 1 mol of alcohol and 4 mol of ketone (as shown in Table 1). The mixture was refluxed for 30 minutes. Subsequently the ketone was removed by distillation, and the level of liquid in the reactor was kept constant by feeding in dry ketone continuously. The progress of the reaction was followed by gas chromatography. The reaction was stopped after the required conversion had been reached by adding 0.1 mol % (based on alcohol) of sodium methanolate. The excess ketone was then removed by distillation.

The purity of the final products was determined by gas chromatography. The reaction times and further data on the final products are shown in Table 1. The amount of dry ketone fed in was shown in the Examples to be about 8 to 15 parts by weight of ketone per 1 part by weight of alcohol.

TABLE 1

(Examples according to the invention)

| Example | Alcohol | Ketone | Reaction time (h) | Yield of final product (%) |
|---|---|---|---|---|
| 1 | Glycerol | Acetone | 9 | 97.6 |
| 2 | Glycerol | Acetone | 12 | 99.5 |
| 3 | Glycerol | 2-Butanone | 12 | 97.0 |
| 4 | Trimethylolpropane | Acetone | 9 | 98.7 |
| 5 | Ethylene glycol | Acetone | 8 | 99.1 |

Comparative Examples 1 and 2 (based on reference [6])

1. 552 g (6 mol) of glycerol, 1392 g (24 mol) of acetone, 1400 g of petroleum ether (boiling range 30 to 75° C.) and 0.47 g (0.05 mol % based on glycerol) of p-toluenesulfonic acid monohydrate were mixed and heated to the boiling point of the solvents. The water of reaction was removed by means of a water trap. After 42 hours, no further water separated out in the water trap. The reaction was stopped by adding 0.94 g of sodium methanolate, and the solvents were removed in a rotary evaporator under reduced pressure. The reaction mixture contained the required product in a yield of 92.5%.

2. 792 g (6 mol) of trimethylolpropane, 1392 g (24 mol) of is acetone, 1400 g of petroleum ether (boiling range 30 to 75° C.) and 0.47 g of p-toluenesulfonic acid monohydrate were mixed and heated to the boiling point of the solvents. The water of reaction was removed by means of a water trap. After 14 hours, no further water separated out in the water trap. The reaction was stopped by adding 0.94 g of sodium methanolate, and the solvents were removed in a rotary evaporator under reduced pressure. The reaction mixture contained the required product in a yield of 91.5%.

REFERENCES

[1] J. Kempe und G. Kiessling, Z. Chem. 26 (1986)3, 97
[2] ES 499 129 A1
[3] EP 456 073 B1
[4] A. Piasecki, Polish Journal of Chemistry 58 (1984), 1215
[5] J. Rübner und H. Frommelt, Mitteilungsbl. Chem. Ges. DDR 31 (1984), 56
[6] M. S. Newman und N. Renoll, J. Amer. Chem. Soc. 67 (1945), 1621
[7] PL 63 823
[8] E. Fischer und E. Pfähler, Ber. Dt. Chem. Ges. 53 (1920), 1027
[9] R. Aldo Macchi, T. Crespo, Rev. Argent. Gras. Aceites 9 [2] (1972), 9
[10] Meng Shen Cai et al., Synth. Commun. 22 (1992) 18,2653
[11] DD 238 232 A1
[12] DD 238 233 A1

We claim:

1. A process for preparing cyclic acetals or ketals by reacting a polyol with an excess of an aldehyde or a ketone having 1 to 6 carbon atoms, in the presence of an acid catalyst, wherein part of the aldehyde or ketone is distilled out during the reaction and wherein the aldehyde or ketone distilled out is replaced by fresh aldehyde or ketone having a water content less than or equal to 1%.

2. A process as claimed in claim 1, wherein a diol or triol having 2 to 12 carbon atoms, in particular ethylene glycol, propylene glycol, glycerol or trimethylolpropane, is used as polyol.

3. A process as claimed in claim 1, wherein an aldehyde or ketone whose boiling point under atmospheric pressure is less than 110° C. and, in particular, less than 100° C. is used.

4. A process as claimed in claim 3, wherein acetone or 2-butanone is used as ketone.

5. A process as claimed in claim 1, wherein from 2 to 30 mol of aldehyde or ketone are employed per mole of polyol.

* * * * *